(12) United States Patent
Stiggelbout

(10) Patent No.: US 9,877,714 B2
(45) Date of Patent: Jan. 30, 2018

(54) SYSTEM WITH RELOADABLE HANDLE FOR DELIVERING AN ANCHOR

(71) Applicant: Neotract, Inc., Pleasanton, CA (US)

(72) Inventor: John Stiggelbout, Sausalito, CA (US)

(73) Assignee: NeoTract, Inc., Pleasanton, CA (US)

( * ) Notice: Subject to any disclaimer, the term of this patent is extended or adjusted under 35 U.S.C. 154(b) by 732 days.

(21) Appl. No.: 14/296,284

(22) Filed: Jun. 4, 2014

(65) Prior Publication Data
US 2015/0351743 A1    Dec. 10, 2015

(51) Int. Cl.
*A61B 17/10*    (2006.01)
*A61B 17/04*    (2006.01)
A61B 17/00    (2006.01)
A61B 17/06    (2006.01)
A61B 90/00    (2016.01)

(52) U.S. Cl.
CPC .... *A61B 17/0401* (2013.01); *A61B 17/00234* (2013.01); *A61B 2017/00022* (2013.01); *A61B 2017/0046* (2013.01); *A61B 2017/00407* (2013.01); *A61B 2017/00849* (2013.01); *A61B 2017/0409* (2013.01); *A61B 2017/0417* (2013.01); *A61B 2017/0419* (2013.01); *A61B 2017/0464* (2013.01); *A61B 2017/0496* (2013.01); *A61B 2017/061* (2013.01); *A61B 2090/0811* (2016.02)

(58) Field of Classification Search
None
See application file for complete search history.

(56) References Cited

U.S. PATENT DOCUMENTS

| | | | | |
|---|---|---|---|---|
| 5,470,010 A | * | 11/1995 | Rothfuss | A61B 17/0644 227/177.1 |
| 5,582,615 A | * | 12/1996 | Foshee | A61B 17/2909 606/139 |
| 5,582,616 A | * | 12/1996 | Bolduc | A61B 17/064 606/139 |
| 6,572,626 B1 | * | 6/2003 | Knodel | A61B 17/0643 606/139 |
| 9,504,461 B2 | * | 11/2016 | Catanese, III | A61B 17/00234 |
| 9,579,090 B1 | * | 2/2017 | Simms | A61B 17/00234 |
| 9,724,080 B2 | * | 8/2017 | Corrao | A61B 17/0057 |
| 2002/0068947 A1 | * | 6/2002 | Kuhns | A61B 17/064 606/143 |
| 2002/0087170 A1 | * | 7/2002 | Kuhns | A61B 17/064 606/143 |
| 2005/0006434 A1 | * | 1/2005 | Wales | A61B 17/07207 227/180.1 |
| 2005/0070925 A1 | * | 3/2005 | Shelton, IV | A61B 17/07207 606/142 |
| 2005/0070958 A1 | * | 3/2005 | Swayze | A61B 17/07207 606/219 |
| 2007/0049948 A1 | * | 3/2007 | Menn | A61B 17/128 606/142 |
| 2007/0049950 A1 | * | 3/2007 | Theroux | A61B 17/128 606/142 |

(Continued)

*Primary Examiner* — Amy R Weisberg
(74) *Attorney, Agent, or Firm* — Christopher J. Buchko

(57) ABSTRACT

An anchor delivery system configured for single patient, multiple use applications. The system includes reloading linkages which cooperate with needle, suture and anchor subassemblies and devices. Reloading actions accomplish the acceptance of a subsequent anchor cartridge and the readying of delivery structure.

12 Claims, 20 Drawing Sheets

(56) References Cited

U.S. PATENT DOCUMENTS

| | | | |
|---|---|---|---|
| 2010/0023022 A1* | 1/2010 | Zeiner | A61B 17/0401 606/139 |
| 2010/0023024 A1* | 1/2010 | Zeiner | A61B 17/0401 606/144 |
| 2010/0023025 A1* | 1/2010 | Zeiner | A61B 17/0401 606/144 |
| 2010/0023026 A1* | 1/2010 | Zeiner | A61B 17/0401 606/144 |
| 2010/0030262 A1* | 2/2010 | McLean | A61B 17/0401 606/232 |
| 2010/0082046 A1* | 4/2010 | Harris | A61B 17/0401 606/139 |
| 2010/0292710 A1* | 11/2010 | Daniel | A61B 17/0401 606/142 |
| 2011/0082471 A1* | 4/2011 | Holcomb | A61B 17/0401 606/139 |
| 2013/0035698 A1* | 2/2013 | Stone | A61B 17/0401 606/139 |
| 2013/0274799 A1* | 10/2013 | Catanese, III | A61B 17/00234 606/232 |
| 2013/0296889 A1* | 11/2013 | Tong | A61B 17/00234 606/139 |
| 2014/0257339 A1* | 9/2014 | Levy | A61B 17/068 606/139 |
| 2014/0257340 A1* | 9/2014 | Ostrovsky | A61B 17/068 606/139 |
| 2014/0330290 A1* | 11/2014 | Tong | A61B 17/0401 606/139 |
| 2014/0379001 A1* | 12/2014 | Cohn | A61B 17/064 606/139 |
| 2015/0351743 A1* | 12/2015 | Stiggelbout | A61B 17/0401 606/144 |
| 2017/0035410 A1* | 2/2017 | Catanese, III | A61B 17/00234 |

* cited by examiner

SYSTEM WITH RELOADABLE HANDLE FOR DELIVERING AN ANCHOR

BACKGROUND

The present disclosure relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner end of the prostate gland to squeeze the urethra. This pressure on the urethra increases resistance to urine flow through the end of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery, and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethral Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry lower risks of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for lifting and repositioning of tissues. However, further advances are necessary to ensure an ability to effectively treat BPH.

There remains a need for the development of new devices and methods that can be used to deploy multiple anchors from a single patient use delivery device to optimize efficiency and efficacy. An ability to access anatomy with minimally invasive instruments while effectively treating a patient is desirable.

The present disclosure addresses these and other needs.

SUMMARY

Briefly and in general terms, the present disclosure is directed towards an apparatus and method for providing a single patient, multiple use system for deploying an anchor assembly within a patient's body to accomplish interventional treatments. A multiple use delivery device is provided to access the anatomy targeted for the interventional procedure. Some embodiments of the delivery device include mechanisms configured to deploy one or more anchor assemblies using a single patient use device system and multiple cartridge assemblies.

The delivery apparatus of the present disclosure includes various subassemblies that are mobilized via an actuator or other manually accessible structure. The operation of the subassemblies is coordinated and synchronized to ensure accurate and precise implantation of an anchor assembly. In one embodiment, the delivery device is embodied in a tissue approximation assembly that is configured to treat BPH.

In particular, in one aspect, the delivery apparatus is configured to accommodate replaceable cartridges. The replaceable cartridges house one or more components of an anchor assembly. The delivery device further includes a handle configured to cooperate with the cartridge as well as a needle assembly, a suture assembly and a proximal anchor assembly. One or more reloading techniques or pulley systems cooperate with a reloading lever to reload each of the needle assembly, suture assembly and proximal anchor assembly components and supporting structure. The handle also embodies structure configured to time the advancement and retraction of the needle assembly with suture assembly tensioning and proximal anchor delivery.

In one methodology, an anchor cartridge assembly is removed from a handle assembly of an anchor delivery apparatus. A suture spring is compressed with a spring follower and a needle spring is compressed by retraction of a needle spring follower. Next, a proximal anchor spring and sled is compressed and reset.

A replacement cartridge is placed within the handle assembly and the device is readied for anchor deployment. Reloading of the cartridge can be accomplished by pulling a reloading lever. Such action results in setting a needle spring and a proximal anchor spring. The reloading lever can then be replaced into a closed position. Reloading of the needle assembly is activated by manipulating a needle trigger. Further depression of the trigger accomplishes needle retraction and tension of the suture. A separate action is used to release the proximal anchor into engagement within the suture.

In another particular aspect, the present disclosure is directed towards a delivery device that accomplishes the delivery of a first or distal anchor assembly component at a first location within a patient's body and the delivery of a second or proximal anchor assembly component at a second location within the patient. Further, the delivery device can include mechanisms for efficient reloading of anchor assembles to minimize patient discomfort and enhance ease of use. The device can also accomplish imparting tension during delivery to a connector to hold it while attaching the proximal anchor in situ. The procedure can be viewed employing a scope inserted in the device. The scope can assume various configurations and can be employed with complementary structure assisting in the viewing function. Also, the delivery device can be sized and shaped to be compatible inside a sheath up to 24 F, preferably a 19 F or 20 F sheath or smaller.

The anchor assembly can be configured to accomplish approximating, retracting, lifting, compressing, supporting, remodeling, or repositioning tissue within the body of a human or animal subject. Moreover, the apparatus configured to deploy the anchor assembly as well as the anchor assembly itself are configured to complement and cooperate with body anatomy.

In one aspect, a system for treating a prostate includes a cartridge, a handle configured to receive the cartridge, and a delivery assembly. The cartridge includes a distal anchor, a connector, and a proximal anchor and the handle includes an actuator and a spring mechanism loaded with mechanical energy. The delivery assembly includes a member that mates with the cartridge to transfer the mechanical energy from the spring mechanism to the cartridge and the actuator operates to reload the mechanical energy.

In one embodiment, a system for deploying an anchor assembly includes a cartridge carrying the anchor assembly and a handle configured to couple with the cartridge such that mechanical energy loaded in at least one spring mechanism within the handle is transferred to the cartridge to deploy the anchor assembly. The system includes an actuator configured to initiate transfer of the mechanical energy and restore the majority of the mechanical energy to the spring mechanisms.

A method for delivering a plurality of anchor assemblies includes inserting a cartridge into a handle assembly is also contemplated. The handle assembly includes an actuator and a drive mechanism having a first loaded configuration characterized by a total stored energy and an unloaded configuration. Operating the actuator simultaneously delivers at least one anchor assembly to the prostate by transferring load from the drive mechanism to the cartridge.

Various alternative methods of use are contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has myriad other potential surgical, therapeutic, cosmetic or reconstructive applications, such as where a tissue, organ, graft or other material requires approximately, retracting, lifting, repositioning, compression or support.

Other features and advantages of the present disclosure will become apparent from the following detailed description, taken in conjunction with the accompanying drawings, which illustrate, by way of example, the principles of the invention.

DETAILED DESCRIPTION OF THE PREFERRED EMBODIMENTS

Turning now to the figures, which are provided by way of example and not limitation, the present disclosure is directed to a device configured to deliver multiple anchor assemblies within a patient's body for treatment purposes. The disclosed apparatus can be employed for various medical purposes including but not limited to retracting, lifting, compressing, approximating, supporting, remodeling, or repositioning tissues, organs, anatomical structures, grafts or other material found within a patient's body. Such tissue manipulation is intended to facilitate the treatment of diseases or disorders such as the displacement, compression and/or retraction of the body tissue.

In an aspect of the present disclosure, the delivery device includes a handle assembly supporting an elongate member. The elongate member defines a low profile that is suited to navigate body anatomy to reach an interventional site. Substructure is provided to maintain a longitudinal profile of the elongate member so that the interventional procedure can progress as intended.

In another aspect, one portion of an anchor assembly or implant is positioned and implanted against a first section of anatomy. A second portion of the anchor assembly or implant is then positioned and implanted adjacent to a second section of anatomy for the purpose of retracting, lifting, compressing, approximating, supporting, remodeling, or repositioning the second section of anatomy with respect to the first section of anatomy as well as for the purpose of retracting, lifting, compressing, approximating, supporting, remodeling, or repositioning the first section of anatomy with respect to the second section of anatomy. It is also to be recognized that both a first and second portion of the anchor assembly can be configured to accomplish the desired retracting, lifting, compressing, approximating, supporting, remodeling, or repositioning of anatomy due to tension supplied during delivery via a connector assembly affixed to the first and second portions of the anchor assembly or implant. The delivery device can include an endoscope providing the ability to view the interventional procedure.

Figure 1A:
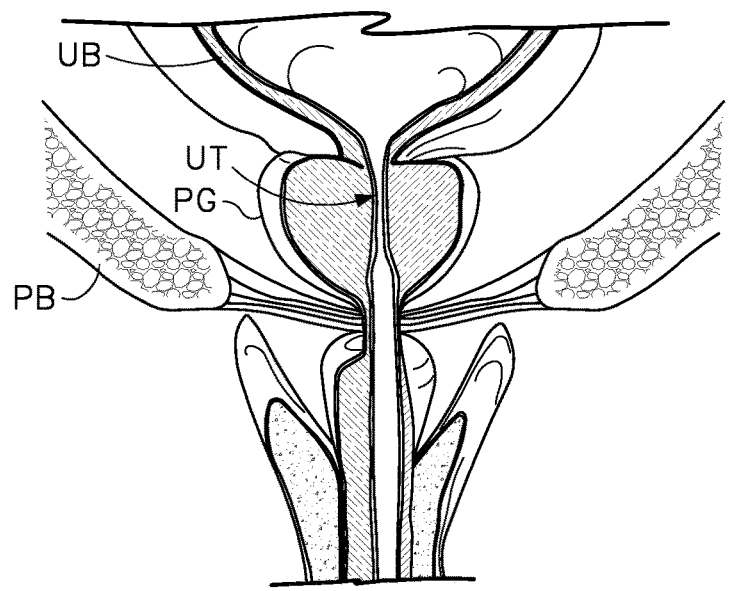
FIG. 1A shows a coronal section through the lower abdomen of a male human suffering from BPH showing a hypertrophied prostate gland.

FIG. 1A shows a coronal section (i.e., a section cut approximately in the plane of the coronal suture or parallel to it) through the lower abdomen of a male human suffering from BPR showing a hypertrophied prostate gland. As depicted in FIG. 1A, the urinary bladder UB is a hollow muscular organ that temporarily stores urine. It is situated behind the pubic bone PB. The lower region of the urinary bladder has a narrow muscular opening called the bladder neck, which opens into a soft, flexible, tubular organ called the urethra UT. The muscles around the bladder neck are called the internal urethral sphincter. The internal urethral sphincter is normally contracted to prevent urine leakage. The urinary bladder gradually fills with urine until full capacity is reached, at which point the sphincters relax. This causes the bladder neck to open, thereby releasing the urine stored in the urinary bladder into the urethra. The urethra conducts urine from the urinary bladder to the exterior of the body. The urethra begins at the bladder neck and terminates at the end of the penis. The prostate gland PG is located around the urethra at the union of the urethra and the urinary bladder. In FIG. 1A, the prostate gland is hypertrophied (enlarged). This causes the prostate gland to press on a region of the urethra. This in turn creates an undesired obstruction to the flow of urine through the urethra.

Figure 1B:
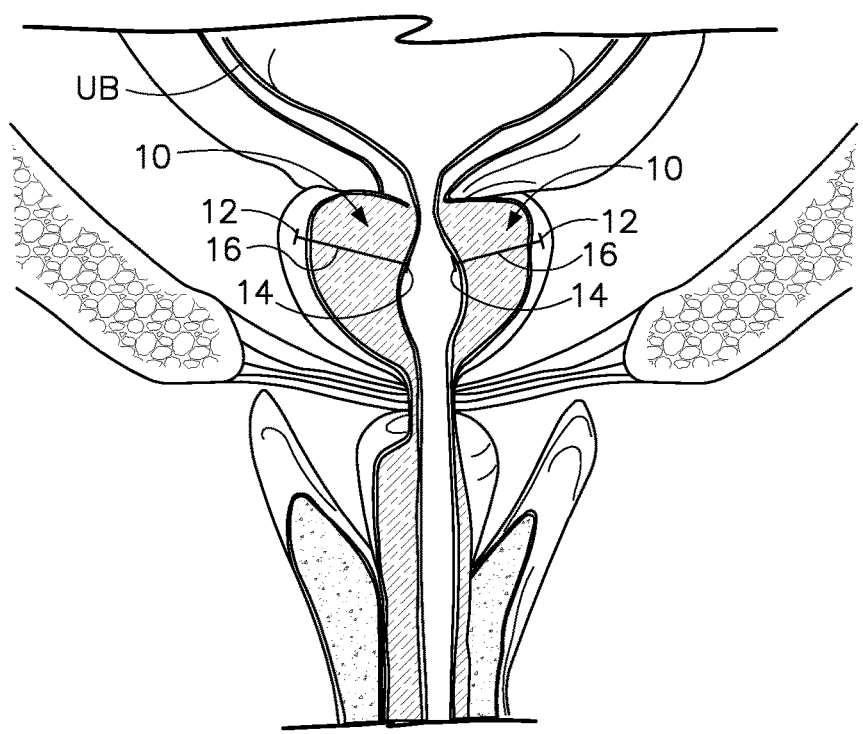
FIG. 1B shows a coronal section through the lower abdomen of a male human suffering from BPH showing a hypertrophied prostate gland treated with an embodiment of the device of the present invention.

FIG. 1B shows a coronal section through the lower abdomen of a male human suffering from BPH showing a hypertrophied prostate gland treated with an embodiment of the device of the present invention. It has been discovered that the enlarged prostate gland is compressible and can be retracted so as to relieve the pressure from the urethra. In accordance with one embodiment of the present invention, a retaining device can be placed through the prostate gland in order to relieve the pressure on the urethra. In FIG. 1B, a retainer 10 is implanted in the prostate gland. Retainer 10 comprises a distal anchor 12 and a proximal anchor 14. Distal anchor 12 and a proximal anchor 14 are connected by a connector 16. The radial distance from the urethra to distal anchor 12 is greater than the radial distance from the urethra to proximal anchor 14. The distance or tension between the anchors is sufficient to compress, displace or change the orientation of an anatomical region between distal anchor 12 and proximal anchor 14. The connector 16 can be inelastic so as to maintain a constant force or distance between the proximal and distal anchors or be elastic so as to attempt to draw the proximal and distal anchors closer together. In the embodiment shown in FIG. 1B, distal anchor 12 is located on the outer surface of the capsule of prostate gland CP and acts as a capsular anchor. Alternatively, distal anchor 12 may be embedded inside the tissue of prostate gland PG or in the surrounding structures around the prostate such as periostium of the pelvic bones, within the bones themselves, pelvic fascia, coopers ligament, muscles traversing the pelvis or bladder wall. Also, in the embodiment shown in FIG. 1B, proximal anchor 14 is located on the inner wall of urethra UT and acts as a urethral anchor. Alternatively, proximal anchor 14 may be embedded inside the tissue of prostate gland PG or surrounding structures as outlined above. Distal anchor 12 and proximal anchor 14 are implanted in the anatomy such that a desired distance or tension is created in connector 16. This causes distal anchor 12 and proximal anchor 14 to retract or compress a region of prostate gland PG to relieve the obstruction shown in FIG. 1A. In FIG. 1B, two retainers 10 are implanted in prostate gland PG. Each retainer 10 is implanted in a lateral lobe (side lobe) of prostate gland PG. The various methods and devices disclosed herein may be used to treat a single lobe or multiple lobes of the prostate gland or other anatomical structures. Similarly, two or more devices disclosed herein may be used to treat a single anatomical structure. For example, a lateral lobe of prostate gland PG may be treated using two retainers 10. One or more retainers may be deployed at particular angles to the axis of the urethra to target one or more lateral lobes and/or middle lobe of the prostate gland. In one embodiment, retainer 10 is deployed between the 1 o'clock and 3 o'clock position relative to the axis of the urethra to target the left lateral lobe of the prostate gland. In another embodiment, retainer 10 is deployed between the 9 o'clock and 11 o'clock position relative to the axis of the urethra to target the right lateral lobe of the prostate gland. In another embodiment, retainer 10 is deployed between the 4 o'clock and 8 o'clock position relative to the axis of the urethra to target the middle lobe of the prostate gland.

Figure 1C:
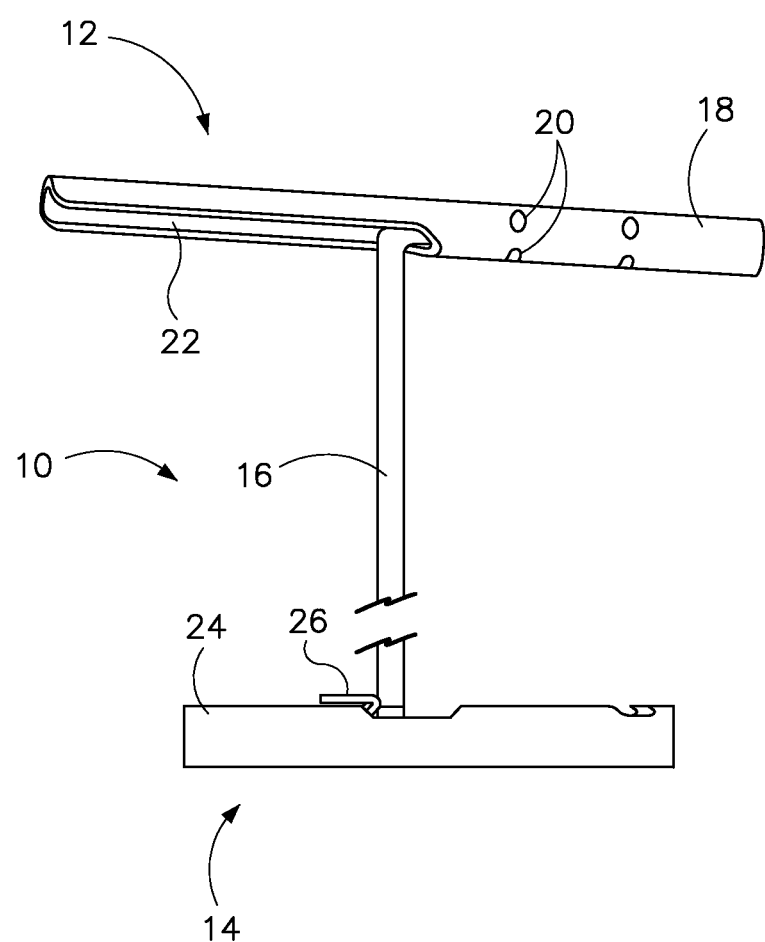
FIG. 1C shows a side view of an embodiment of the retainer shown in FIG. 1B.
Figure 1D:
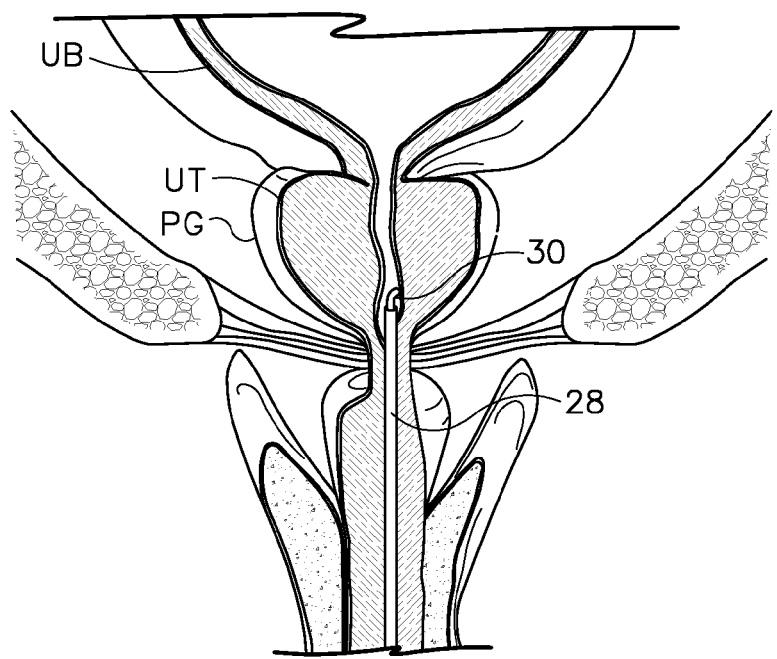
FIGS. 1D through 1I show the various steps of a method of treating a prostate gland by the retainer shown in FIG. 1C.

FIG. 1C shows a side view of one embodiment of the retainer shown in FIG. 1B. FIG. 1C shows retainer 10 comprising distal anchor 12 and proximal anchor 14. Distal anchor 12 and proximal anchor 14 are connected by connector 16. In the embodiment shown in FIG. 1C, distal anchor 12 comprises a tube 18 having a lumen. Tube 18 can be made of suitable elastic or nonelastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, EPTFE, shape memory polymers, such as polyesterurethane, polyetherurethane, polyetherpolyesters, polyetherpolyamines or combinations of oligo ecaprolactore diol and oligo p-dioxanone diol polymers, etc. Connector 16 is attached to tube 18. In one embodiment, connector 16 is a USP size 0 polypropylene monofilament suture. In the embodiment shown in FIG. 1C, a distal region of connector 16 is located in the lumen of tube 18 such that the distal tip of connector 16 emerges out of one end of the lumen of tube 18. The distal tip of connector 16 is enlarged, such that the diameter of the enlarged distal tip of connector 16 is greater than the inner diameter of tube 18. In one embodiment, the diameter of connector 16 is 0.014 inches and the diameter of the enlarged distal tip of connector 16 is 0.025 inches. In one embodiment, the enlarged distal tip of connector 16 is created by controlled melting of the distal tip of connector 16. This attaches connector 16 to tube 18. Tube 18 may comprise one or more additional attachment mechanisms to attach a distal region of connector 16 to tube 18. In one embodiment, the distal region of connector 16 is attached to tube 18 by a suitable biocompatible adhesive. In the embodiment shown in FIG. 1C, the distal region of connector 16 is attached to tube 18 by one or more inwardly opening flaps 20 that are cut in the material of tube 18. Flaps 20 grip connector 16 and thus prevent the relative motion of connector 16 and tube 18. The angle between one of flaps 20 and connector 16 may range from 1 degree to 90 degrees. Tube 18 further comprises a longitudinal slot 22. Longitudinal slot 22 extends from one end to roughly the mid section of tube 18. Connector 16 emerges out of this longitudinal slot 22. Thus, when connector 16 is pulled in the proximal direction, distal anchor 12 assumes a T-shape that helps to anchor distal anchor 12 to an anatomical structure. Distal anchor 12 may comprise a sharp edge to help penetrate distal anchor 12 through the anatomy. In a preferred embodiment, distal anchor 12 is constructed by laser cutting and electropolishing a nickel-titanium alloy (e.g., nitinol) tube made of 50.8% nickel-49.2% titanium. In the preferred embodiment, the outer diameter of tube 18 is 0.026 inches, the inner diameter of tube 18 is 0.015 inches, the length of tube 18 is 0.315 inches and the length of longitudinal slot 22 is 0.170 inches.

Figure 1E:
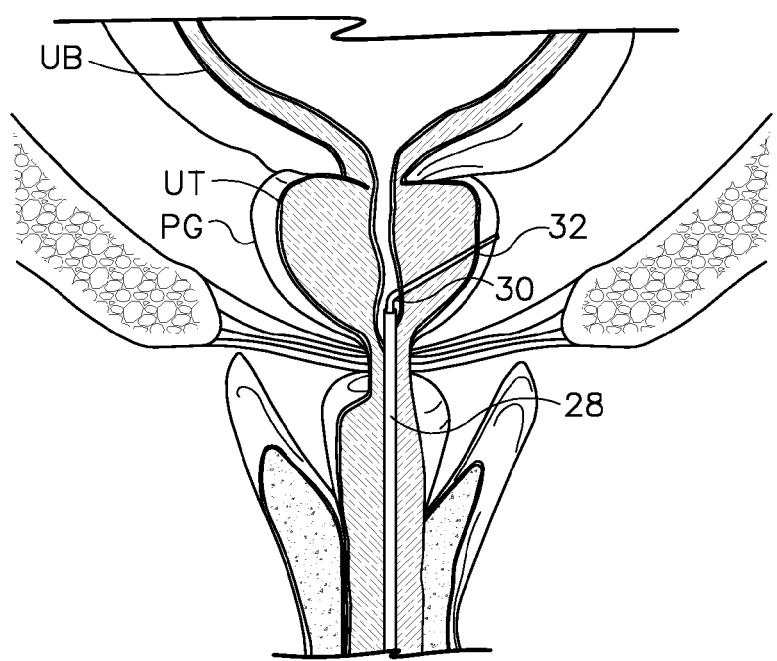

In the embodiment shown in FIG. 1C, proximal anchor 14 comprises a tube 24 comprising a lumen. Tube 24 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, ePTFE, such as polyesterurethane, polyetherurethane, polyetherpolyesters, polyetherpolyamines or combinations of oligo e-caprolactone diol and oligo p-dioxanone diol polymers, etc. An outwardly opening flap 26 is cut through the material of tube 24. Flap 26 is folded on the outer surface of tube 18 as shown in FIG. 1E. This creates an opening to the lumen of tube 24 that is lined by the atraumatic edge of the folded flap 26. Connector 16 enters tube 24 through this opening to the lumen of tube 24. Proximal anchor 14 further comprises an attachment mechanism to attach connector 16 to tube 24. Connector 16 can be made of suitable elastic or non-elastic materials including, but not limited to metals, polymers, etc. Other proximal anchor and distal anchor concepts are within the scope of the invention, such as v-shaped proximal anchors that are press fit onto a connector. Typical examples of such materials include, but are not limited to stainless steel 304, stainless steel 316, nickel-titanium alloys, suture materials, titanium, silicone, nylon, polyamide, polyglycolic acid, polypropylene, Pebax, PTFE, ePTFE, silk, gut, or any other braided or mono-filament material. In a preferred embodiment, tube 24 has a length of 0.236 inches and an outer diameter of 0.027 inches and an inner diameter of 0.020 inches. The length of opening to the lumen of tube 24 is approximately 0.055 inches. In the preferred embodiment, the attachment mechanism comprises a lock pin that frictionally attaches connector 16 to tube 24. The lock pin and tube 24 are made of stainless steel 316L. In the preferred embodiment, tube 24 is laser cut or stamped and then electropolished. Lock pin is constructed using EDM (electrical discharge machining) and then passivated.

FIGS. 1D through 1J show the various steps of a method of treating a prostate gland by the retainer shown in FIG. 1C. Similar methods may be also used to deploy retainer or compression devices in other anatomical structures. In the step shown in FIG. 1D, a sheath 28 such as a standard resectoscope sheath is introduced into the urethra (transurethrally). Sheath 28 is advanced through urethra UT such that the distal end of sheath 28 is positioned near a region of urethra UT that is obstructed by a hypertrophied prostate gland PG. Distal anchor delivery device 30 is introduced through sheath 28. Distal anchor delivery device 30 can be placed in the sheath 28 after the distal end of sheath 28 is positioned near the region of the urethra UT that is obstructed or the distal anchor delivery device 30 can be pre-loaded in the sheath 28 before positioning of the sheath 28. Distal anchor delivery device 30 is advanced through sheath 28 such that the distal end of distal anchor delivery device 30 emerges out of the distal end of sheath 28. Distal anchor delivery device 30 is oriented such that a working channel opening of distal anchor delivery device 30 points towards a lateral lobe of prostate gland PG.

In the step shown in FIG. 1E, a needle 32 is introduced through distal anchor delivery device 30. Needle 32 can be placed in distal anchor delivery device after the distal anchor delivery device 30 is advanced through sheath 28 or the needle 32 can be pre-loaded in the distal anchor delivery device 30. In one embodiment, needle 32 is a 20 gauge needle. Needle 32 is advanced through distal anchor delivery device 30 such that it emerges through the working channel opening. Needle 32 is further advanced such that it penetrates through the tissue of prostate gland PG and the distal end of needle 32 emerges out of the capsule of prostate gland CP.

Figure 1F:
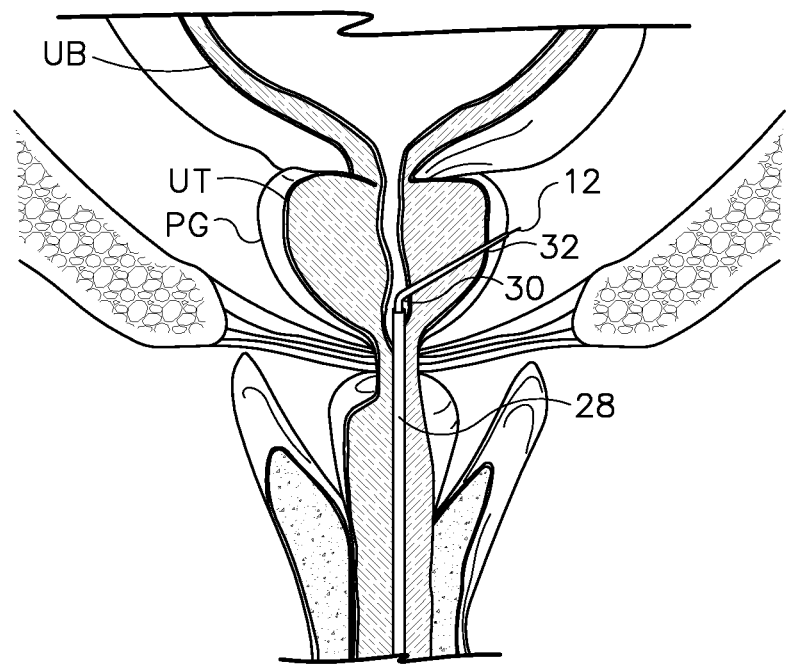

In the step shown in FIG. 1F, distal anchor 12 connected to connector 16 is advanced through needle 32. Distal anchor 12 can be pre-loaded in needle 32 or can be loaded in needle 32 after needle 32 has been advanced through distal anchor delivery device 30. Distal anchor 12 is advanced through needle 32 such that it emerges out of the distal end of needle 32. In alternate embodiments, the distal anchor can be held in place by a pusher or connector while the needle is retracted, thus exposing the distal anchor.

Figure 1G:
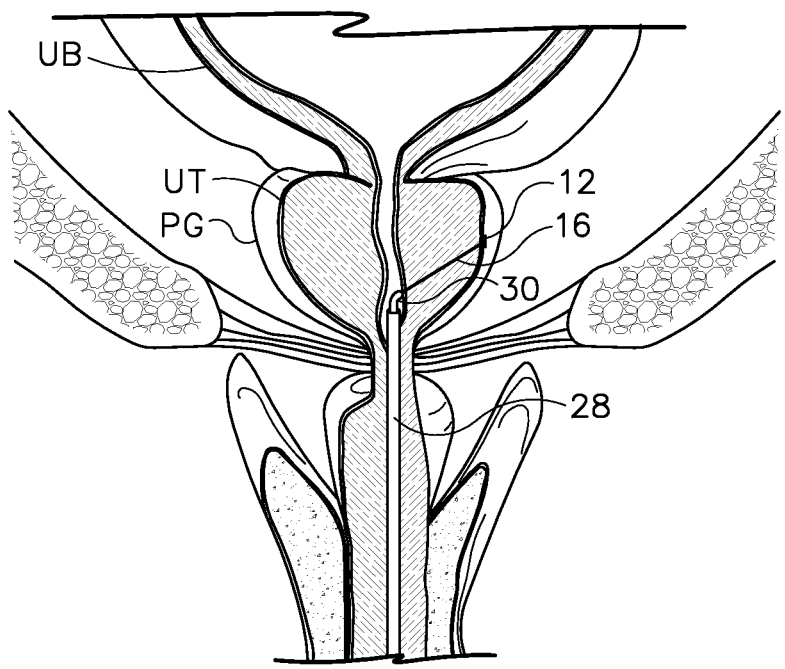

In the step shown in FIG. 1G, needle 32 is removed from distal anchor delivery device 30 by pulling needle 32 in the proximal direction.

Figure 1H:
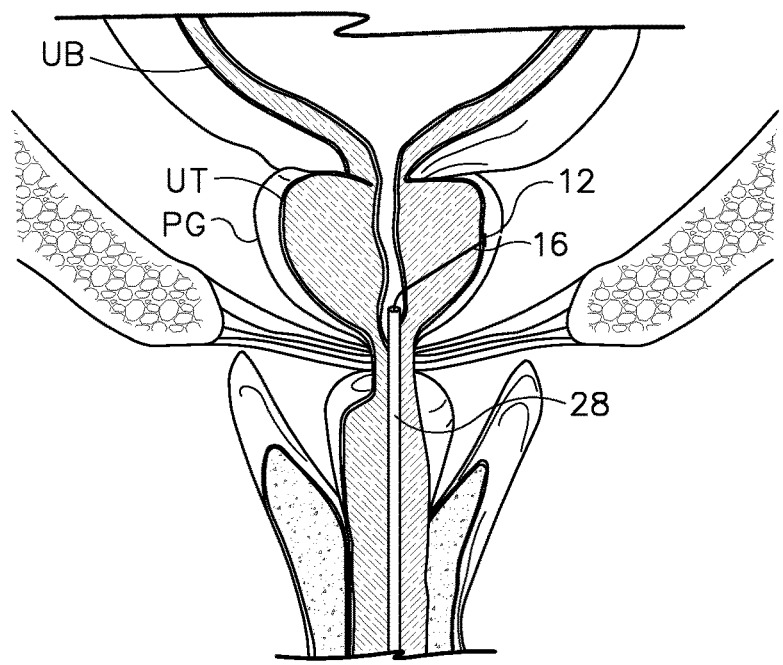

In the step shown in FIG. 1H, distal anchor delivery device 30 is removed from sheath 28 by pulling distal anchor delivery device 30 in the proximal direction. Also, connector 16 is pulled to orient distal anchor 12 perpendicularly to connector 16.

Figure 1I:
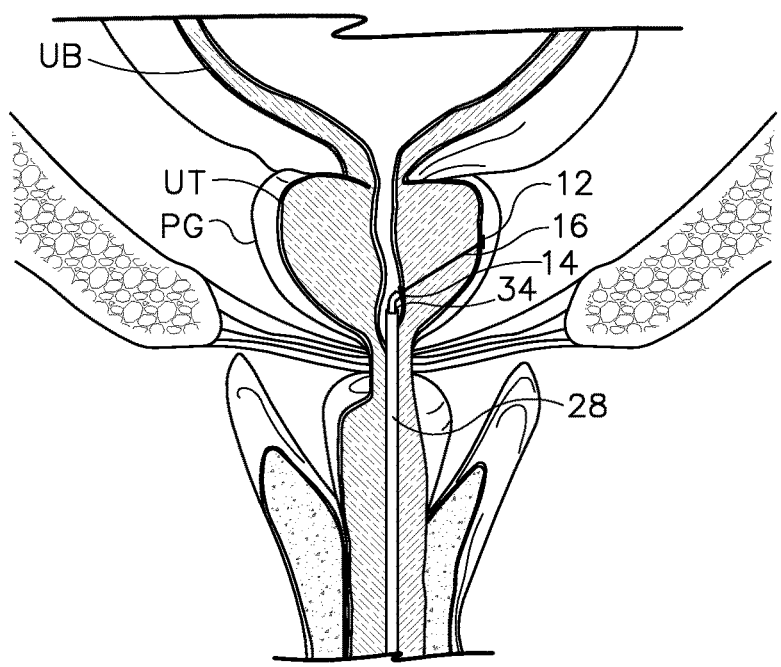

In the step shown in FIG. 1I, connector 16 is passed through proximal anchor 14 located on a proximal anchor delivery device 34. Proximal anchor delivery device 34 is advanced through sheath 28 such that the distal end of proximal anchor delivery device 34 emerges out of the distal end of sheath 28. A desired tension is introduced in connector 16 such that distal anchor 12 is pulled by connector 16 with a desired force. Alternatively, the proximal anchor can be visualized through an endoscope or under fluoroscopy and advanced along the connector until the desired retraction of the tissue is achieved. In other embodiments, the proximal anchor is a v-shaped or clothespin-shaped piece that is forced, in some cases at high speed, onto the connector to fixedly engage the connector.

Figure 1J:
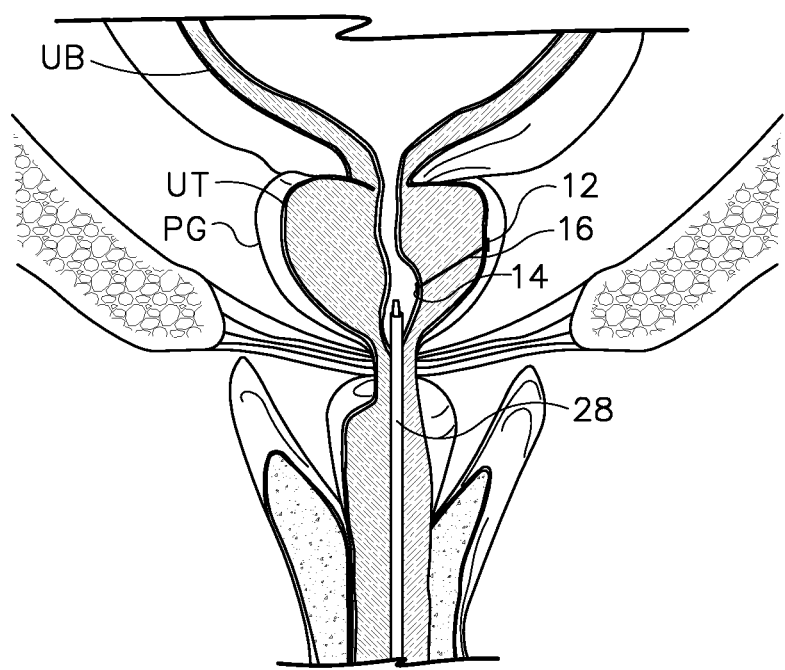

In the step shown in FIG. 1J, connector 16 is attached to proximal anchor 14. Proximal anchor 14 is also released from proximal anchor delivery device 34, thus deploying proximal anchor 14 in the anatomy. Proximal anchor delivery device 34 and sheath 28 are removed from the anatomy. Retainer 10 comprising distal anchor 12, proximal anchor 14 and connector 16 is used to retract, lift, support, reposition or compress a region of prostate gland PG located between distal anchor 12 and proximal anchor 14. This method may be used to retract, lift, support, reposition or compress multiple regions or lobes of the prostate gland PG. In the method shown in FIGS. 1D through 1J, distal anchor 12 is deployed on the outer surface of the capsule of prostate gland CP. Thus, distal anchor 12 acts as a capsular anchor. Alternatively, distal anchor 12 may be deployed inside the tissue of prostate gland PG or beyond the prostate as outlined previously. Similarly, in the method shown in FIGS. 1D through 1I, proximal anchor 14 is deployed on the inner wall of urethra UT and acts as a urethral anchor. Alternatively, proximal anchor 14 may be deployed inside the tissue of prostate gland PG.

The tissue approximation anchor shown in FIG. 1C is designed to be useable in a physician's clinical office environment (in contrast to requiring a hospital environment) with a delivery tool. The delivery tool is used through a 19 F or 20 F sheath in one preferred embodiment. Additionally, the material selection and construction of the tissue approximation anchor still allows for a subsequent TURP procedure to be performed, if necessary, on the prostate. In this suture-based, tissue approximation technique, a needle delivery mechanism is used to implant an anchor assembly.

Figure 2:
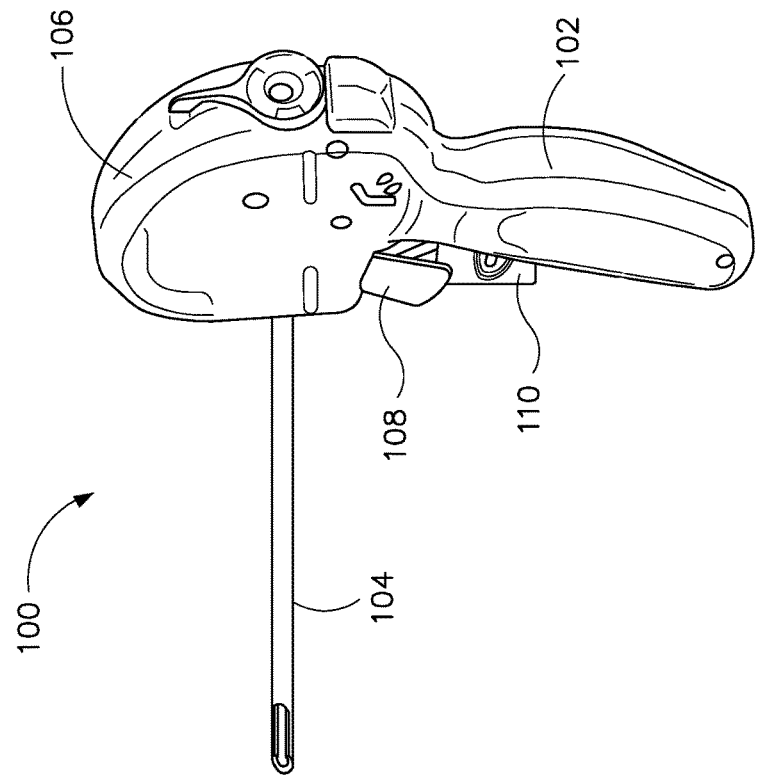
FIG. 2 is a perspective view depicting one embodiment of an anchor delivery system.
Figure 3:
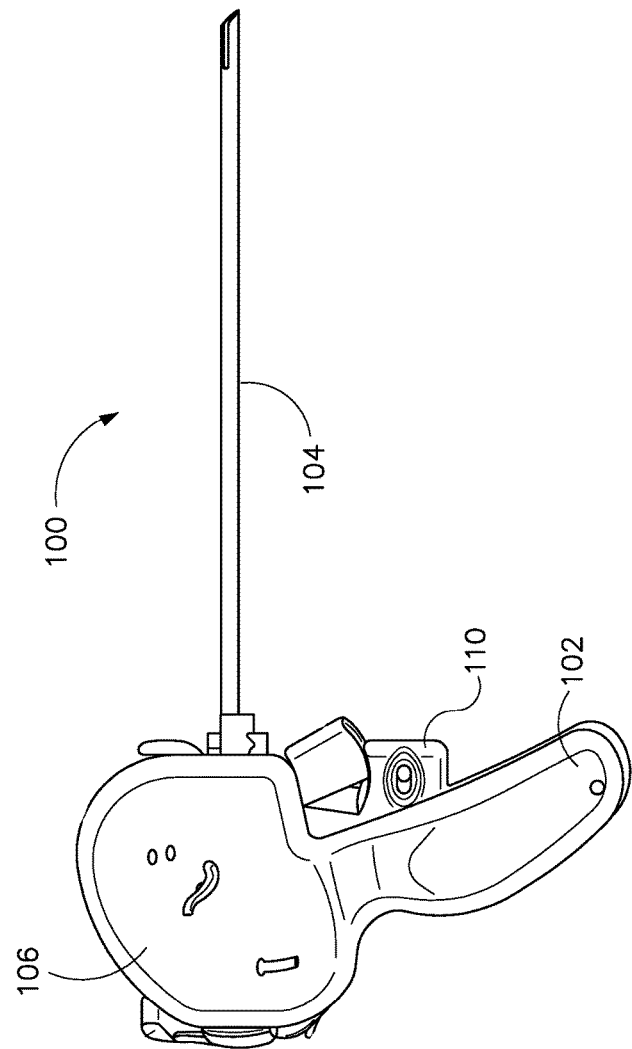
FIG. 3 is a right side view depicting the anchor delivery system of FIG. 2.
Figure 4:
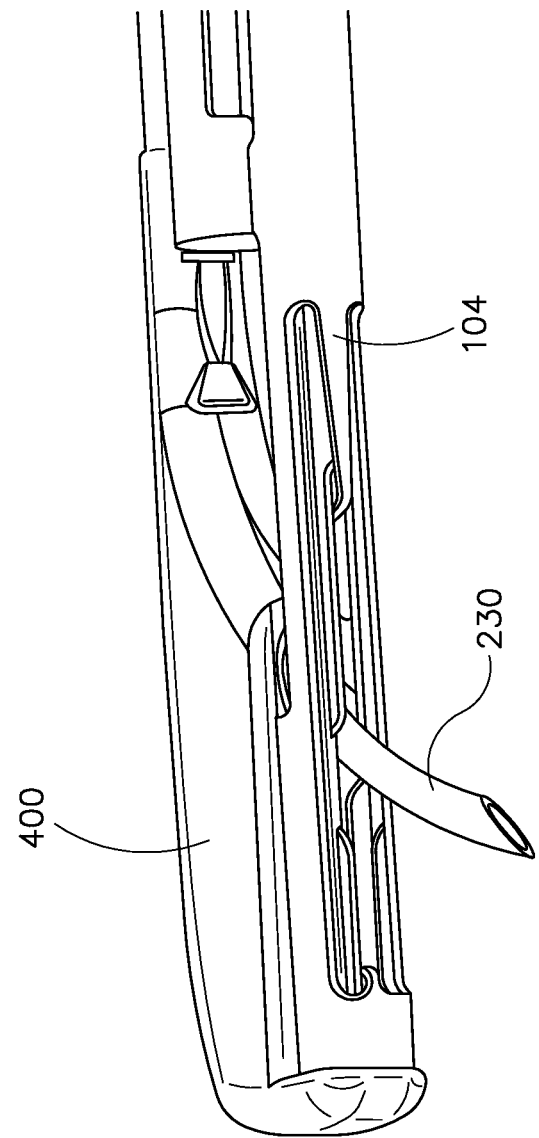
FIG. 4 is a perspective view in partial cross-section depicting partial advancement of a needle assembly.

Referring now to FIGS. 2-4, there is shown one embodiment of a delivery device 100. This device is configured to include structure that is capable of both gaining access to an interventional site as well as assembling and implanting one or more anchor assemblies or implants within a patient's body. The delivery device 100 can be configured to assemble and implant a single anchor assembly or implant a single bodied anchor or multiple anchors or anchor assemblies. The device is further contemplated to be compatible for use with a 19 F or 20 F sheath. The device additionally includes structure configured to receive a conventional remote viewing device (e.g., an endoscope) so that the steps being performed at the interventional site can be observed.

Prior to use of the present device 100, a patient typically undergoes a five day regimen of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to elongate member 104. Elongate member 104 can house components employed to construct an anchor assembly and is sized to fit into a 19 F or 20 F cystosopic sheath for patient tolerance during a procedure in which the patient is awake rather than under general anesthesia. The assembly is intended to include structure to maintain its positioning within anatomy.

The anchor delivery device 100 further includes a number of subassemblies. A handle case assembly 106 includes mating handle parts that form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members that facilitate assembly and delivery of an anchor assembly at an interventional site. A needle actuator 108 is provided and, as described in detail below, effectuates the advancement of a needle assembly to an interventional site. In one approach, the needle assembly moves through a curved trajectory and exits the needle housing in alignment with a handle element, and in particular embodiments, in alignment with the grip. In various other embodiments, the needle housing is oriented such that the needle exits the housing at either the two o'clock or ten o'clock positions relative to a handle grip that is vertical. A needle retraction lever assembly 110 is also provided and when actuated causes the needle assembly to be withdrawn and expose the anchor assembly.

In one particular, non-limiting use in treating a prostate, the elongate member 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate member 104 is advanced within the patient until a leading end thereof reaches a prostate gland (PG). In a specific approach, the side(s) (or lobe(s)) of the prostate to be treated is chosen while the device extends through the bladder and the device is turned accordingly. The inside of the prostate gland, including the adenoma, is spongy and compressible and the outer surface, including the capsule, of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

The delivery device is at this stage configured in a ready state. The needle actuator 108 and the needle retracting lever 110 are in an inactivated position.

Upon depression of the needle actuator 108, the needle 230 (See FIG. 4) is advanced from within the elongate member 104. The needle can be configured so that it curves back toward the handle as it is ejected. In use in a prostate intervention, the needle is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (such as wetness) that may degrade effectiveness of needle penetration.

Certain anchor delivery devices include springs as part of the mechanisms that drive a needle or penetrating member, deploy an anchor, cut a connector, or perform other functions related to device delivery. The devices may include springs that are preloaded with potential energy when the user removes the device from packaging. Preloaded springs can be susceptible to degradation over time when stored in a loaded state, whether that state is tension or compression. Spring degradation may affect a device's shelf life. Also, spring degradation can affect the consistency of the device as the spring force can change over time. Further, loaded components may creep due to constant stress.

Figure 5:
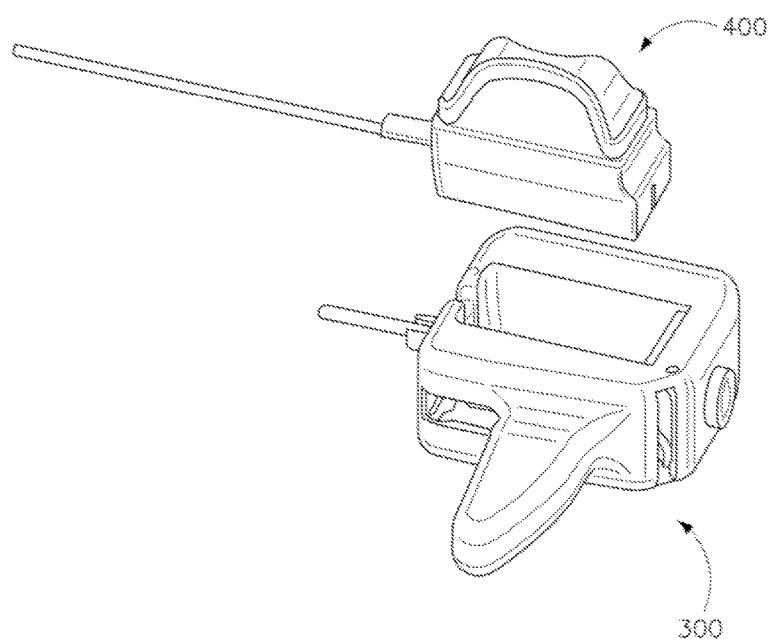
FIG. 5 is a perspective view of an anchor delivery system including a cartridge and a handle.

FIG. 5 illustrates one embodiment of an anchor delivery system 200 including a handle assembly 300 and a cartridge assembly 400. Cartridge assembly 400 is sized, shaped, and configured to couple to handle assembly 300. Cartridge assembly 400 contains one or more anchors, such as retainer 10 depicted in FIG. 1C. Cartridge assembly 400 includes features which mate with features on the handle assembly 300 to transmit mechanical forces from the handle assembly 300 to the cartridge assembly 400. For example, squeezing a lever (not pictured) on handle grip 310 can actuate mechanical forces, such as spring loaded mechanical forces, that are transmitted to the cartridge assembly 400 for deploying an anchor, such as retainer 10.

Figure 6A:
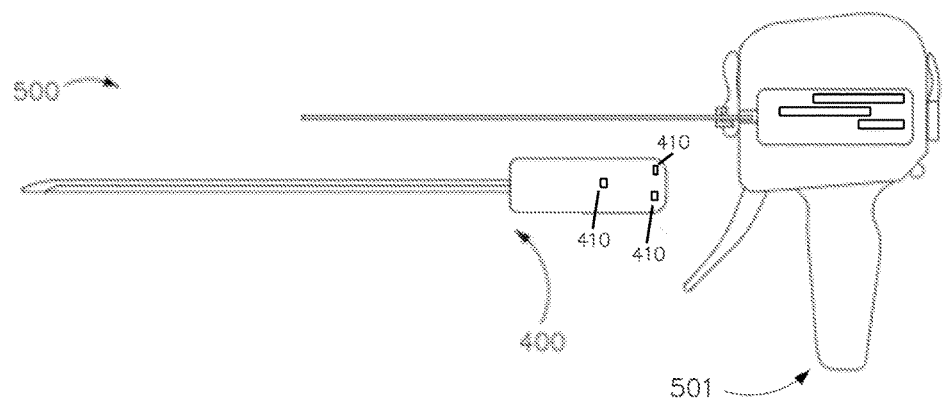
FIG. 6A is a side view of the far side of an anchor delivery system including a cartridge and a handle.
Figure 6B:
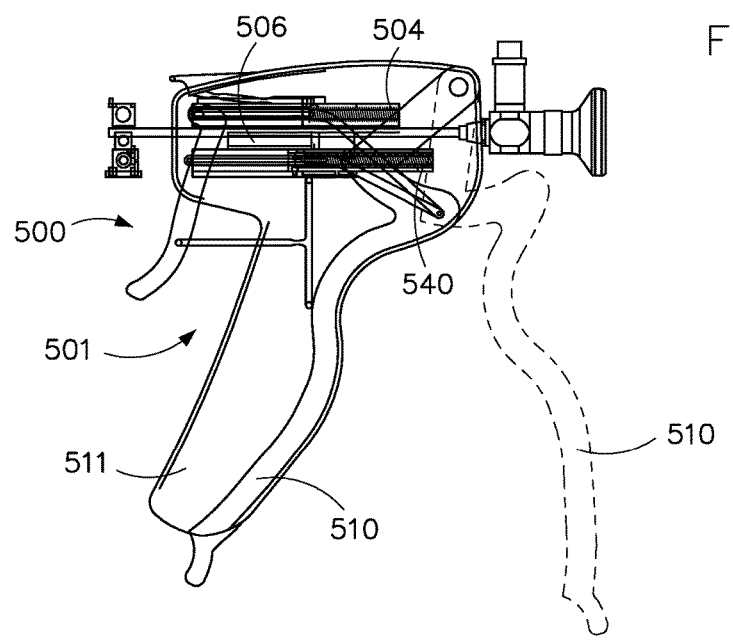
FIG. 6B is a side view with a side cover removed, depicting one approach to a single-patient, multiple sue handle for an anchor delivery system.

Turning now to FIGS. 6A-16, a first approach a single patient, multiple use delivery apparatus 500 is disclosed. In FIG. 6A, the cartridge 400 is attached from the far, rather than the near side of the device. Notably, the cartridge 400 has three sliding tabs 410 which engage the three spring-driven sleds (see FIGS. 9, 13, and 15) incorporated into a handle mechanism 501. Only significant internal parts related to re-cocking are identified in the figures.

Figure 7:
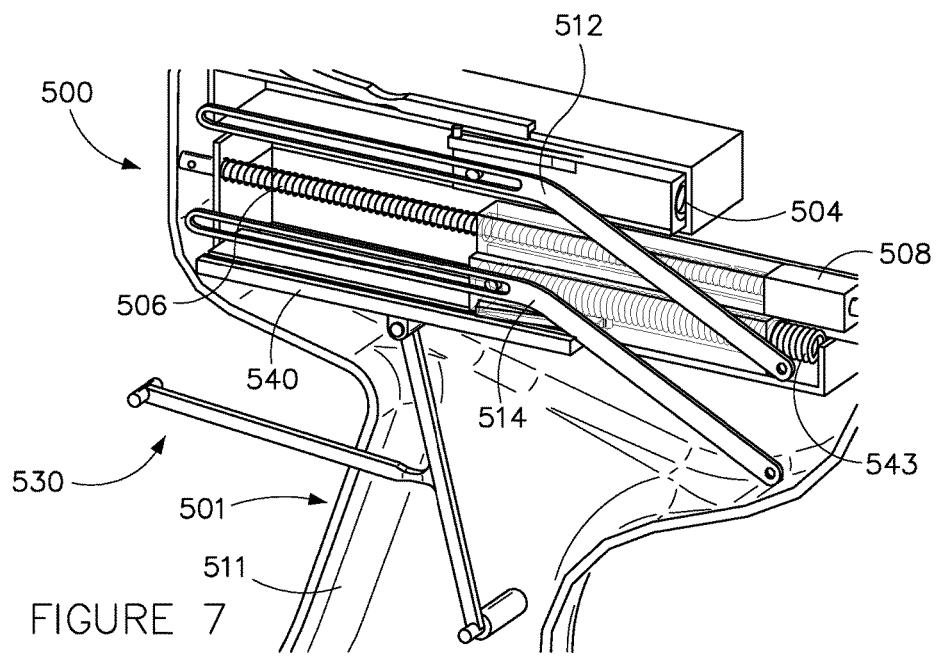
FIG. 7 is a side perspective view, depicting internal components of the system of FIG. 6.
Figure 8:
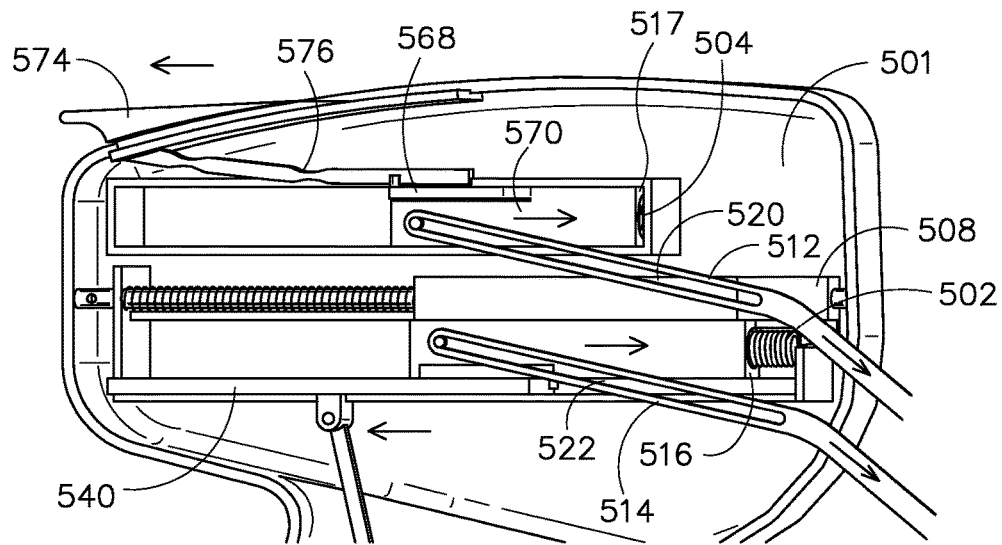
FIG. 8 is a side view, depicting certain internal structure of the system of FIG. 6.
Figure 9:
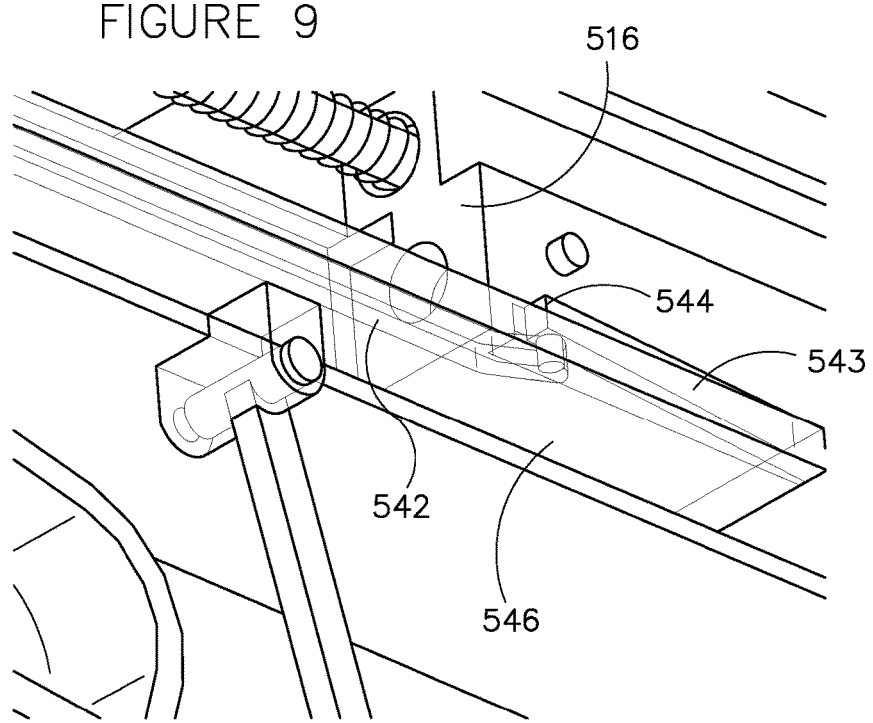
FIG. 9 is an enlarged view, depicting details of a needle spring follower and needle sled of the system of FIG. 6.
Figure 10:
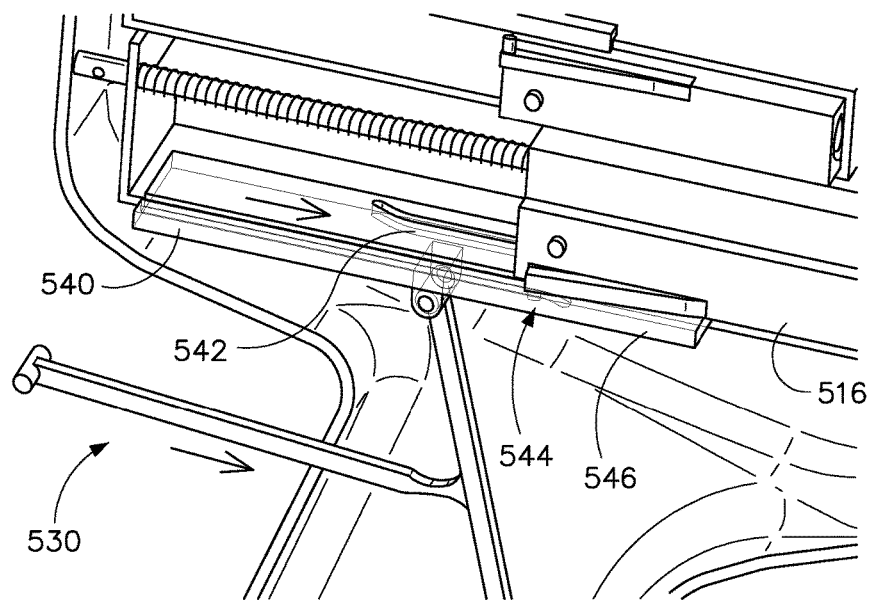
FIG. 10 is a side perspective view, depicting release of a spring follower of the system of FIG. 6.
Figure 11:
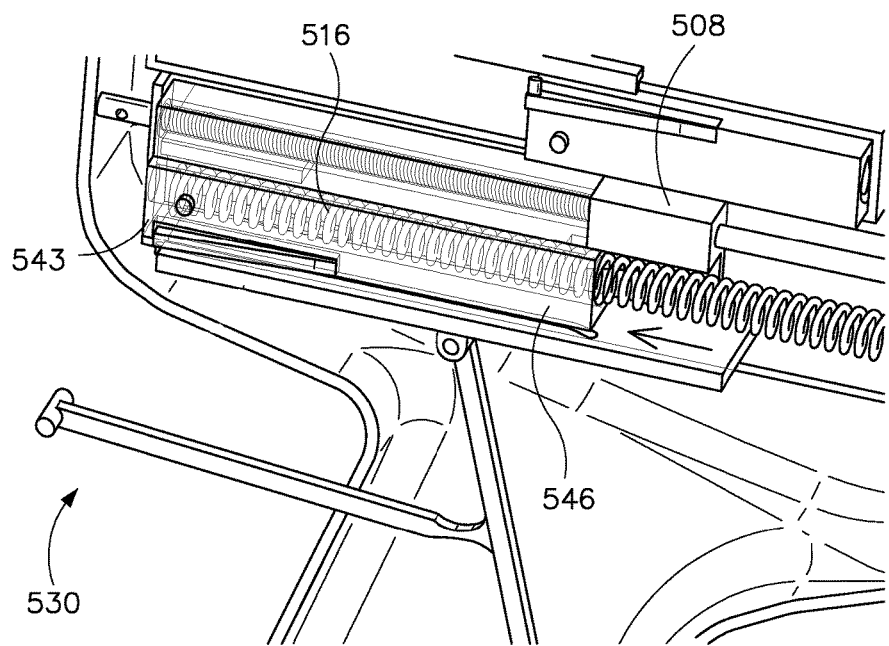
FIG. 11 is a side perspective view, depicting needle deployment action of the system of FIG. 6.

Reloading of the delivery apparatus 500 involves compression and latching of two springs, a needle spring 502 and a proximal anchor or urethral spring 504. A suture spring 506 is compressed with the release of the needle spring 502 which occurs immediately before release of a suture sled 508. Accordingly, the suture spring 506 does not need to be re-compressed at reloading. The reloading action is accomplished by pulling a lever 510 integrated into the back of the handle 501. The user holds the snout 511 of the handle 501 and pulls the tail of the reload lever 510 with his fingertips. Referring in particular to FIG. 8, the pivoting action retracts a pair of slotted linkages 512, 514 which in turn retract a spring follower 516, compressing the needle spring 502 which is latched when it is in its fully retracted position. The same action is used on a proximal anchor spring follower 517 to cock the urethral spring 504. As the reloading lever 510 (See FIG. 6) is closed again, (snapped onto the back of the handle 501), the reloading linkages 512, 514 are returned to their distal position where slots 520, 522 formed therein are distal to the spring followers 516, 517 and parallel to them, as shown in FIG. 7. Release of the followers 516, 517 is unencumbered by the presence of the linkages 512, 514. (They are not shown in subsequent illustrations.)

The device 500 is now ready to accept a new cartridge from the far side (not shown) of the device. Firing of the needle is accomplished by pulling the trigger assembly 530 about 5-6 mm (See FIG. 6). This slides a trigger plate 540 in the proximal direction. A cam slot 542 in the plate 540 deflects pawls (or tabs) on the needle spring follower 516 and needle sled 543 (See also FIGS. 12-14.

As shown, the spring follower 516 has a cylindrical finger 544 which engages a slot 542 in the trigger slider 546 which acts like a cam slot to deflect the finger. The actions are shown by the arrows in FIG. 10. It is to be noted that the follower locking tab engages a notch in the left handle body which is not shown.

Consequently, the trigger slider 546 has been moved 5-6 mm proximally releasing the needle spring follower 516. The needle spring 502 drives the spring follower 516 together with the needle sled and suture sled 508 forward distally the required 1.5" as shown by the arrow (See FIG. 11).

One feature of this system is that the suture spring 506 is compressed by the distal movement of the suture sled 508. This requires that the needle spring 502 be oversized relative to the amount of energy needed to only drive the needle because it needs to provide enough energy to drive the needle and to fully compress the suture spring 506.

Figure 12:
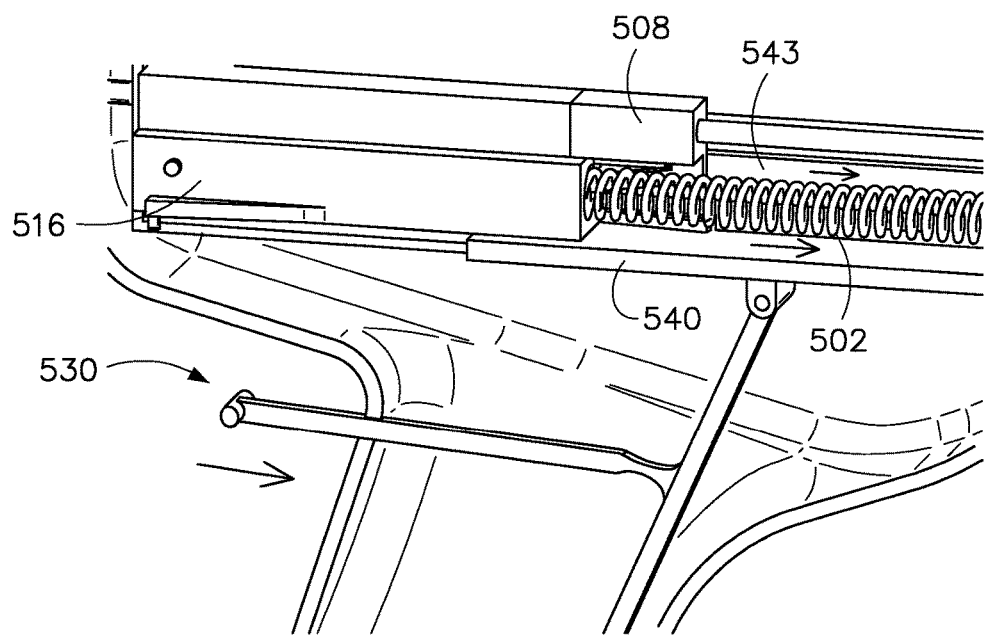
FIG. 12 is a side view, depicting needle retraction of the system of FIG. 6.
Figure 13:
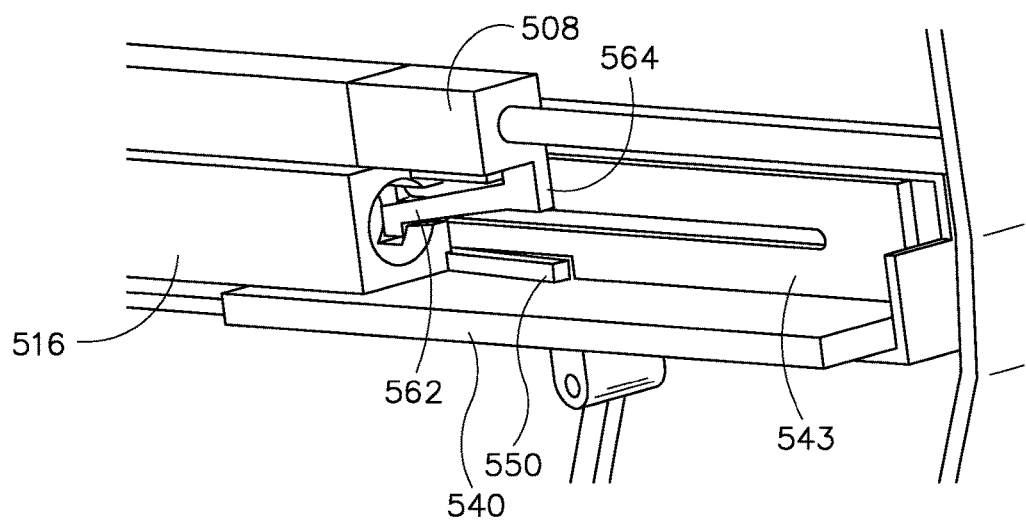
FIG. 13 is an enlarged view, depicting details of a suture sled locking arm of the system of FIG. 6.
Figure 14:
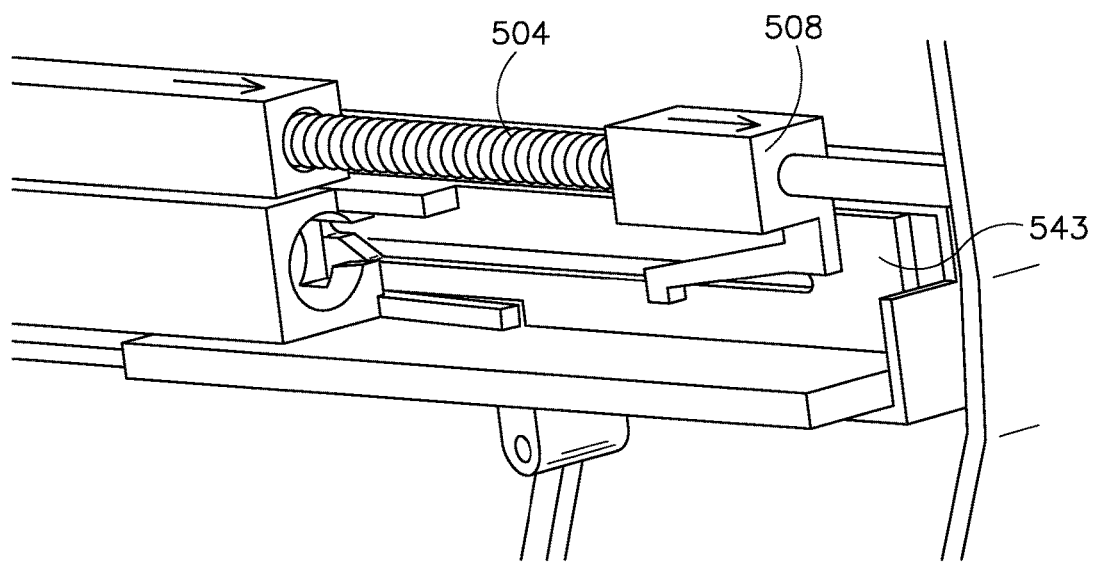
FIG. 14 is an enlarged view, depicting detail of tensioning a suture of the system of FIG. 6.

Referring now to FIGS. 12-14, retraction of the needle sled 543 is described. Here, the needle sled 543 is retracted by the trigger plate 540. A fingered tab on the bottom of the needle sled 543 engages a slot in the trigger plate 540. As the spring follower 516 is driven forward, a pawl (or flexing tab) 550 on the needle sled 543 is disengaged from the spring follower 516 but the finger stays engaged with the trigger plate 540.

Because the needle sled 543 needs to be retracted 1.6" but with relatively low force, a simple stroke multiplying linkage is proposed. The linkage 530 is a combination of lever, flexure and column. The bottom end is fixed in a journal in the handle and the top is attached with a knuckle to the trigger slider. The left end is attached to the needle trigger (not shown). This effectively gives a 2:1 stroke multiplication with a single simple part.

Referring specifically to FIG. 13, the needle spring is hidden to allow view of the engagement arm on the suture sled 508 where it engages the spring follower 516. A finger 562 on an engagement arm 564 rides in a slot in the needle sled 543 keeping it engaged until the needle sled 543 is fully retracted.

Referring in particular to FIG. 14, the needle sled 543 is fully retracted and a cam slot on the end of the sled 543 has lifted the engagement arm 564 on the suture sled 508 out of its notch in the spring follower 516. This allows it to be driven proximally, tensioning the suture.

The subsequent step follows a brief pause, which is distinct and separate from previous actions. A separate slide or button is proposed to initiate this next step. This action is straightforward because there are no other interactions except for re-cocking.

Figure 15:
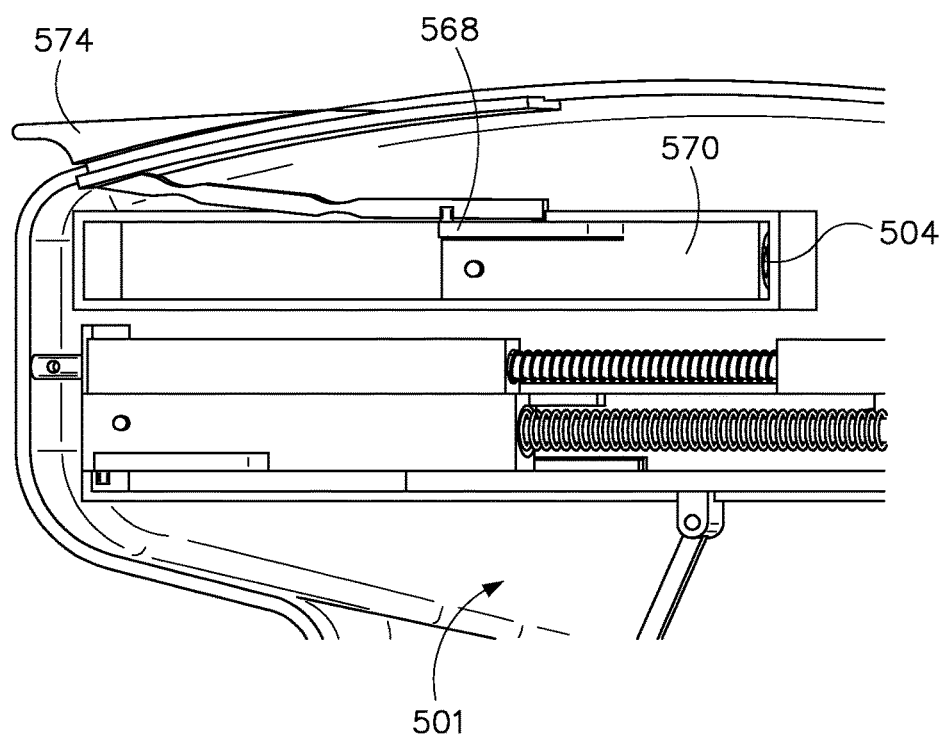
FIG. 15 is a side view, depicting details of an anchor sled of the system of FIG. 6.
Figure 16:
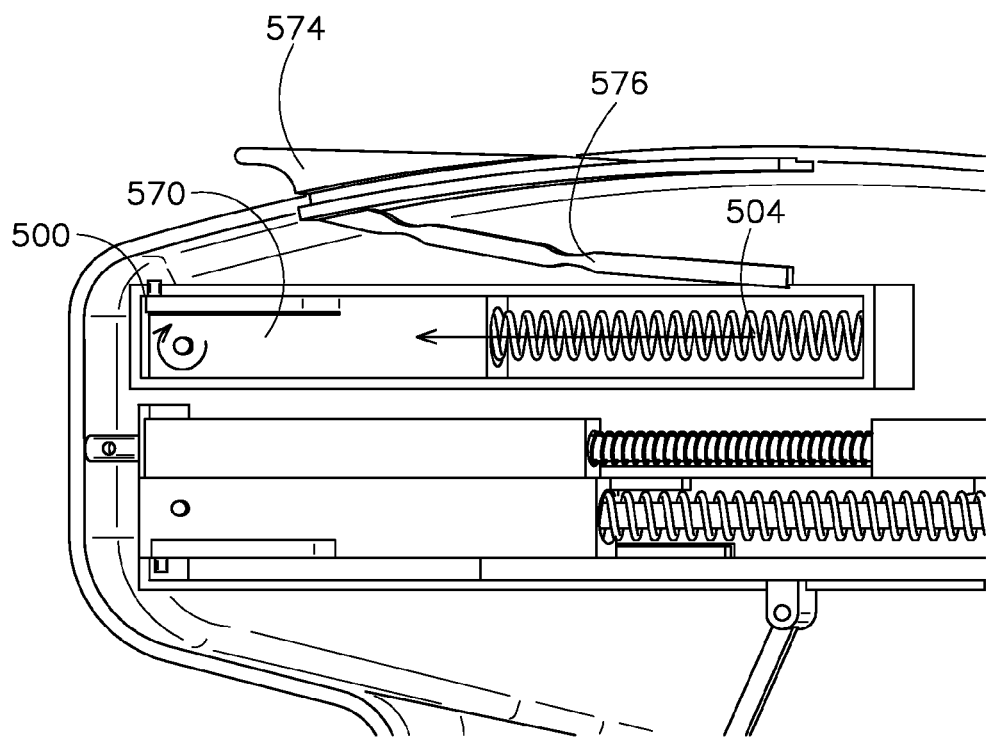
FIG. 16 is a side view, depicting release of the anchor sled of FIG. 15.
Figure 17:
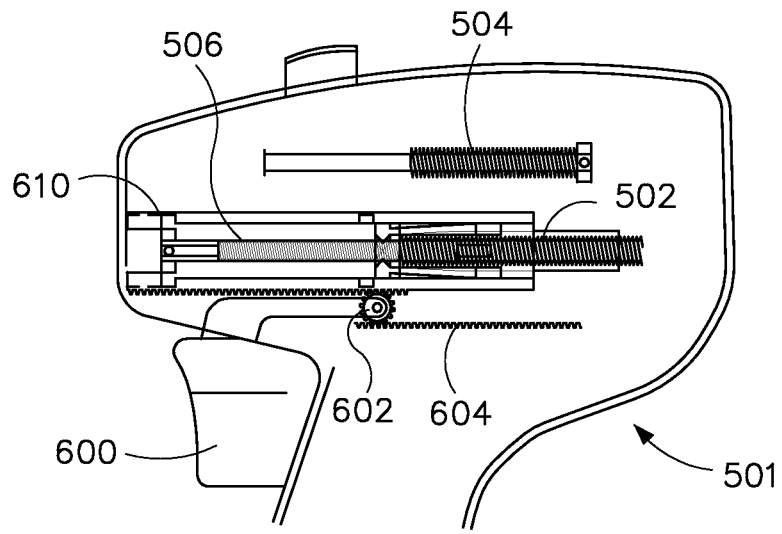
FIG. 17 is a side view, depicting another embodiment of a single-patient, multiple use anchor delivery system.
Figure 18:
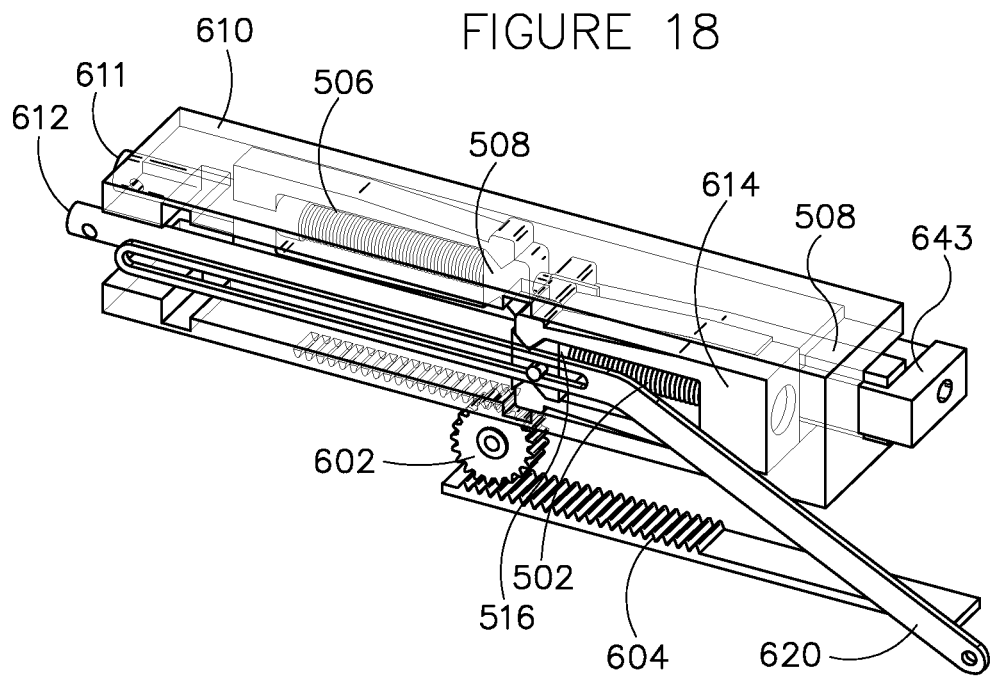
FIG. 18 is a perspective view, depicting internal components of the system of FIG. 17.

Referring to FIG. 15, detail of proximal or urethral anchor activation structure is presented. As above, a flexure 568 is molded in as part of a urethral sled 570 and functions as a pawl or locking tab, holding the urethral spring 504 in compression. A release button 574 can have a slotted cam required to disengage the sled locking tab 568. An arm 576 extending from the release button 574 provides structure for releasably engaging the sled flexion 568. Also, the tab 568 can engage a notch in the handle case. The release button 574 may also require a small return spring (not shown). Thus, sliding the release button operates to disengage the urethral sled 570 from a locked position, thereby allowing the suture spring 504 to advance the urethral sled 570 proximally which in turn accomplishes the advancement of a proximal anchor into engagement with a suture to complete the assembly of an anchor.

A second embodiment of the device is similar in many respects but different in others (See FIGS. 17-23). One parallel, for example, is the use of a sliding trigger 600 connected to a pinion 602 which is meshed with a fixed rack 604 and a trigger sleeve 610, instead of using a lever/linkage stroke multiplier to retract the needle sled. Pulling the trigger 600 advances the pinion shaft 602 which translates into a 2:1 stroke multiplier. One feature of this approach can include mechanical efficiency because spur gears are very efficient due to their inherent rolling action and a compact method of increasing stroke. In this approach, the needle spring 502 and suture spring 506 are situated side-by-side instead of over-under. The urethral spring 504 is still placed above the other two.

The suture spring guide 611 and needle spring guide 612 are anchored in the handle 501 and provide reference for all the sliding features of the mechanism. For example, a needle spring release 614 is attached to the end of the needle spring guide 612. Reloading is identical to the device described above and retraction of the linkage 520 is similar. Here, all actions for releasing the needle, retracting the needle and tensioning the suture are all controlled by retraction of the trigger sleeve 610.

Figure 19:
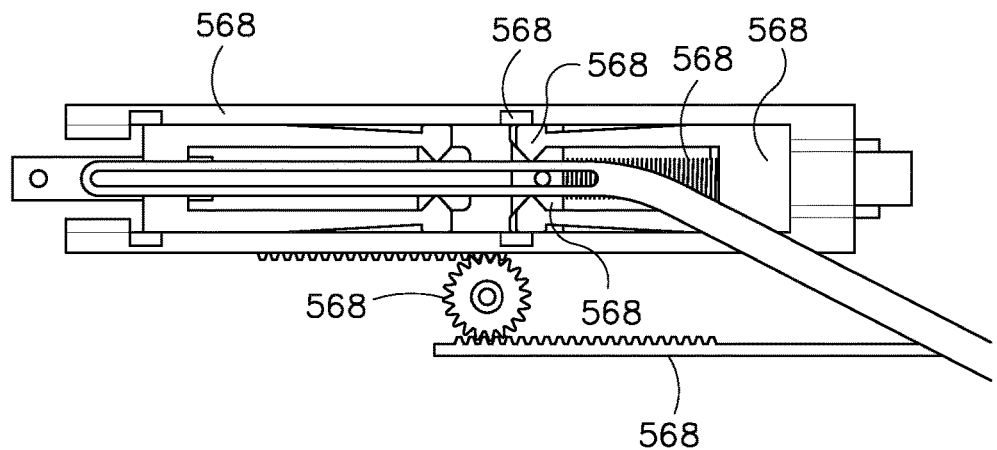
FIG. 19 is a side view, depicting the internal components shown in FIG. 18.
Figure 20:
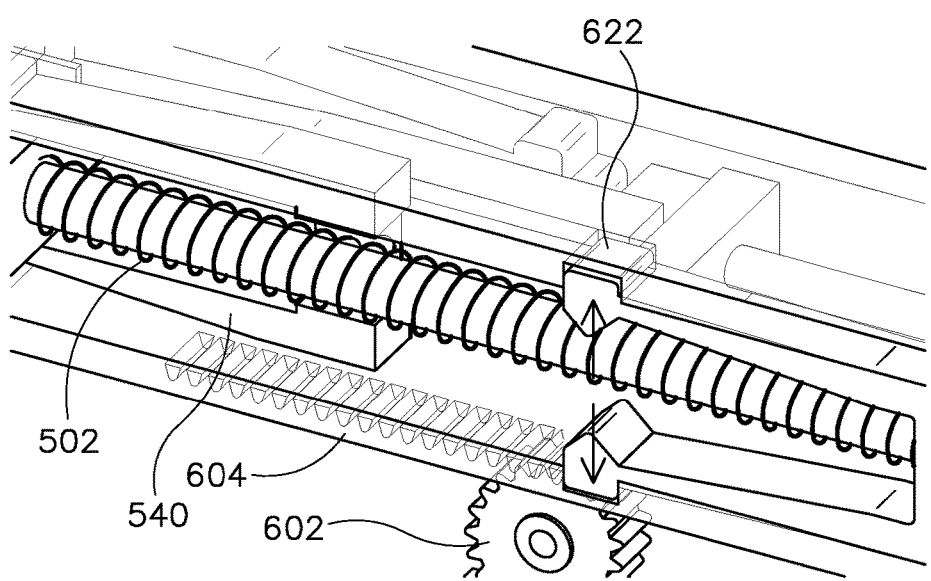
FIG. 20 is an enlarged view, depicting structure involved in a release of a needle spring of the system shown in FIG. 17.

Referring to FIG. 19, the needle spring 502 is held in compression by the needle follower 516 which is restrained by arms 622 of the spring release 614. As the trigger sleeve 610 is moved back about 0.050", the arms 622 drop into notches 624 in the trigger sleeve 610 and splay apart, releasing the spring follower 516. The arms are forced open as shown in FIG. 20 and the spring follower 516 moves forward out of the way.

As soon as the needle spring 520 is driven forward and the needle is deployed, the arms of the spring release 614 snap back in (see arrows in FIG. 21) disengaging the trigger sleeve 610. Almost simultaneous with this, the needle sled 543 is driven forward to the point where its arms align with slots 630 in the end of the trigger sleeve 510 thus allowing it to disengage from the spring follower 516. This is shown by the arrows on the needle sled 543.

Figure 21:
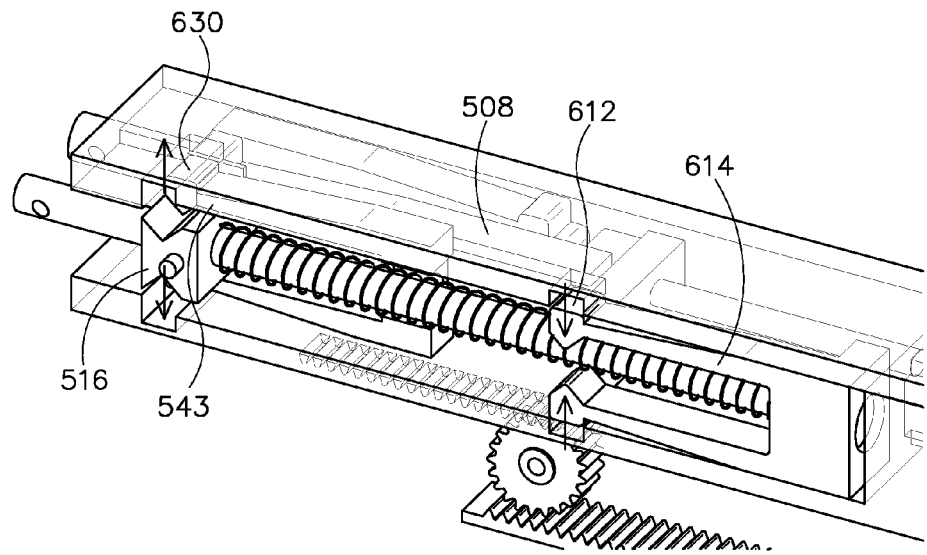
FIG. 21 is an enlarged view, depicting structure involved in engagement and disengagement of a needle sled of the system of FIG. 17.

Still referring to FIG. 21, the arms 622 on the suture spring retainer 614 and the suture sled 508 are held closed by the internal surface of the trigger sleeve 610. It is particularly important that the suture sled 508 be held positively closed and in the distal position for the first few centimeters of needle retraction because this is where the highest friction and binding forces can occur.

Figure 22:
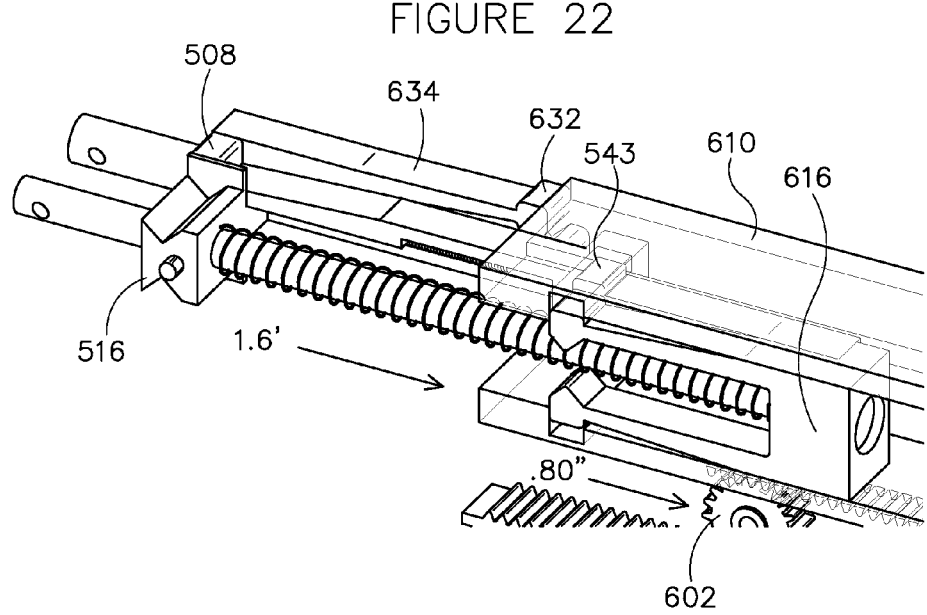
FIG. 22 is an enlarged view, depicting further detail concerning the action of the needle sled.
Figure 23:
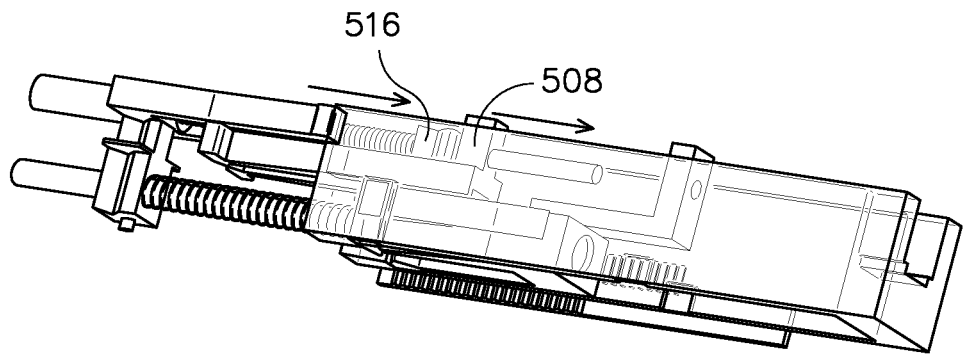
FIG. 23 is a top view, depicting detail of suture tensioning of the system of FIG. 17.

As the trigger sleeve 610 is moved proximally, by retracting the needle sled 543, shown in FIG. 22, the suture sled 508 is no longer held positively in the v-groove of the needle spring follower 516, but it is still engaged by a cantilever force of the arms of the suture sled 508. This allows it to be held in position but also allows it to disengage from the spring follower 516 when the suture spring is released. Also shown in this figure are the distances (1.6 inches vs 0.80 inches) moved of the pinion idler 602 and the trigger sleeve 610.

At the end of travel of the trigger sleeve 610, arms 622 of a suture spring release 134 become disengaged from the trigger sleeve 610. The arms 622 splay open releasing the suture spring follower 516 which contacts the suture sled 508 and thereby pushes it in the proximal direction with the predetermined force. This is shown by the pair of arrows in FIG. 23.

The scheme for releasing the urethral sled and spring can be accomplished by actuation of a slide type button on top of the handle. Reloading of the device is accomplished by completing the a) removal of the spent cartridge; b) compression of the suture spring with the spring follower; c) compression of the needle spring by refraction of the needle spring follower; d) advancement of the trigger sleeve back to its initial position; and e) the urethral spring and sled can be compressed and reset either before or after.

Figure 24:
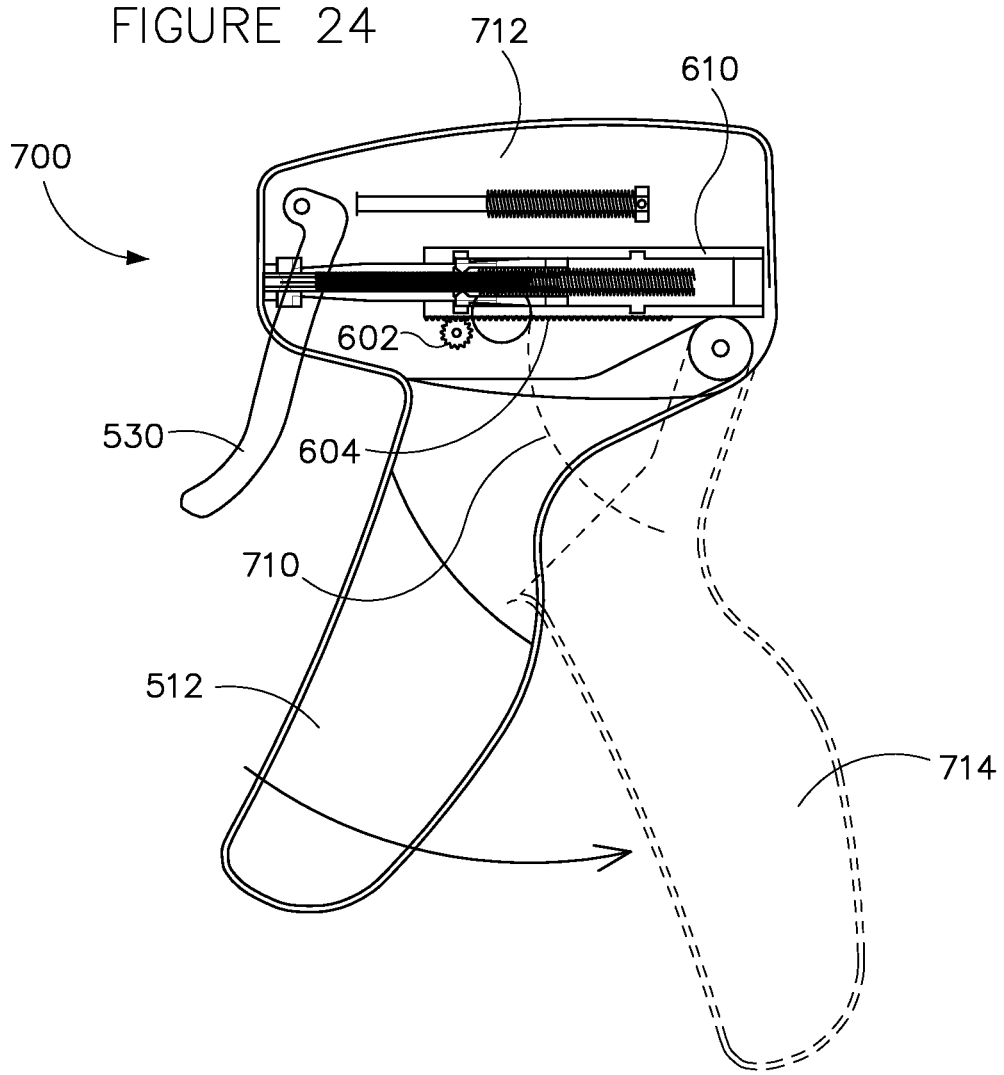
FIG. 24 is a side view, depicting yet another approach to a single-patient, multiple use anchor delivery system.

FIG. 24 shows an alternative handle assembly 700 involving a different scheme for re-cocking springs. Instead of using a set of linkages, this approach incorporates a set of chem-etched steel ribbons or very fine wire rope cables 710 which run over a series of pulleys or wheels thus converting the flexing motion of the handle into linear motion co-axial to the instrument shaft.

The approach here is that the user holds a body 712 of the handle of the device in one hand and snout of the device in the other hand and "pivots" them apart. It is easy to generate both a large force and a large stroke in this way. In this concept, the reloading lever 714 is an integral part of the handle is thus dual-purpose. That is, the lever is used to hold the device in use and to reload it.

The method of use of the anchor delivery system can incorporate the use of a cystoscope, endoscope, or similar visualization device. In some embodiments, the proximal handle includes a scope lock with no moving parts for locking a cystoscope to the handle prior to performing the treatments disclosed herein. The lack of moving parts reduces the cost and increases the reliability and ease of use.

Embodiments described herein provide several advantages, including, but not limited to, the ability to efficiently deliver multiple anchor assemblies while reducing patient discomfort and increasing ease-of-use. Certain embodiments provide mechanisms for, with a single lever or equivalent actuator, delivering an anchor assembly and recharging the stored energy in the delivery device such that the device is ready or near ready to deliver another anchor assembly by simply replacing a cartridge in the delivery system.

Accordingly, the present invention contemplates both pushing directly on anchor portions of an anchor assembly as well as pushing directly upon the connector of the anchor assembly. Moreover, as presented above, the distal or first anchor component can be advanced and deployed through a needle assembly and at least one component of the proximal or second anchor component is advanced and deployed from the needle or from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the displacement, compression, and/or retraction of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure. In one preferred embodiment, the shape and contour of the anchor assembly is configured so that the assembly invaginates within target tissue, such as within folds formed in the urethra by the opening of the urethra lumen by the anchor assembly. In desired placement, wispy or pillowy tissue in the area collapses around the anchor structure. Eventually, the natural tissue can grow over the anchor assembly and new cell growth occurs over time. Such cooperation with target tissue facilitates healing and avoids unwanted side effects such as calcification or infection at the interventional site.

Subsequent to the interventional procedure, the patient can be directed to take appropriate drugs or therapeutic agents, such as alpha blockers and anti-inflammatory medicines.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating that retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors that can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism that pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

I claim:

1. A system for deploying an anchor assembly, comprising:
   a replaceable cartridge carrying the anchor assembly; and
   a handle configured to couple with the replaceable cartridge, wherein the handle includes a reloading linkage cooperating with the cartridge, a needle assembly, a needle release and retraction trigger, a reloading lever, and a proximal anchor delivery structure and wherein the cartridge includes three slide tabs which engage three spring device sleds.

2. The system of claim 1, wherein the handle includes a first reloading linkage cooperating with the needle assembly and a second reloading linkage cooperating with the proximal anchor delivery structure.

3. The system of claim 1, wherein the reloading lever is attached to the reloading linkage.

4. The system of claim 1, wherein the reloading linkage includes a first elongate point and a second elongate point formed at an angle with the first elongate point.

5. The system of claim 4, wherein the first elongate point includes a slot extending substantially an entire length of the first elongate point.

6. The system of claim 5, wherein the slot is sized and shaped to receive a member extending from one or more of a proximal anchor sled and a needle sled.

7. The system of claim 1, wherein reloading of the system involves compression and latching of a needle spring and a proximal anchor spring.

8. The system of claim 1, further comprising a suture spring and a needle spring, wherein the suture spring is compressed upon release of the needle spring.

9. The system of claim 1, further comprising a needle spring and a suture spring, the needle spring and suture spring being arranged laterally side by side.

10. The system of claim 9, further comprising a proximal anchor spring arranged above the needle and suture springs.

11. The system of claim 1, further comprising a suture sled, wherein the suture sled is held in a closed distal position during a first few centimeters of needle assembly retention.

12. The system of claim 1, wherein the proximal anchor is held in a reloaded position until after retraction of the needle assembly.

* * * * *